(12) United States Patent
Larsen

(10) Patent No.: US 11,241,329 B2
(45) Date of Patent: Feb. 8, 2022

(54) OSTOMY DEVICE

(71) Applicant: MULTI-LOCK ApS, Haderslev (DK)

(72) Inventor: Martin Vilhelm Larsen, Vallensbaek Strand (DK)

(73) Assignee: Multi-Lock APS

( * ) Notice: Subject to any disclaimer, the term of this patent is extended or adjusted under 35 U.S.C. 154(b) by 937 days.

(21) Appl. No.: 15/983,735

(22) Filed: May 18, 2018

(65) Prior Publication Data

US 2018/0344506 A1 Dec. 6, 2018

(30) Foreign Application Priority Data

May 31, 2017 (DK) .......................... PA 2017 00325

(51) Int. Cl.
| | | |
|---|---|---|
| *A61F 5/44* | (2006.01) | |
| *A61F 5/441* | (2006.01) | |
| *A61F 5/448* | (2006.01) | |
| *A61F 5/445* | (2006.01) | |

(52) U.S. Cl.
CPC ............ *A61F 5/4407* (2013.01); *A61F 5/441* (2013.01); *A61F 5/445* (2013.01); *A61F 5/448* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,121,589 A | * | 10/1978 | McDonnell | A61F 5/441 604/328 |
| 5,045,052 A | | 9/1991 | Sans | |
| 8,092,437 B2 | * | 1/2012 | Cline | A61F 5/448 604/337 |
| 8,217,221 B2 | * | 7/2012 | Davies | A61F 5/445 604/378 |
| 8,998,867 B2 | * | 4/2015 | Sabeti | A61F 5/4405 604/335 |
| 9,517,157 B2 | * | 12/2016 | Hanuka | A61F 5/445 604/335 |
| 2003/0220621 A1 | | 11/2003 | Arkinstall | |
| 2007/0123832 A1 | * | 5/2007 | Cline | A61F 5/445 604/335 |
| 2013/0030397 A1 | * | 1/2013 | Sabeti | A61F 5/445 604/335 |
| 2013/0116636 A1 | | 5/2013 | Carrubba | |

(Continued)

FOREIGN PATENT DOCUMENTS

| | | |
|---|---|---|
| EP | 1774931 A2 | 4/2007 |
| EP | 1774932 A1 | 4/2007 |

(Continued)

*Primary Examiner* — Guy K Townsend
(74) *Attorney, Agent, or Firm* — Boyle Fredrickson, SC (57) ABSTRACT

An ostomy device (2) for attachment (coupling) to a base plate (6) is disclosed. The ostomy device (2) comprises an attachment ring (8) configured for attachment to the base plate (6). The ostomy device (2) further comprises elements (10, 12, 16) provided with means (18, 48, 78, 80) configured to be detachably attached to the attachment ring (8), and comprises a shield (60) provided with a blocking element (16) for blocking the stoma (20), wherein the blocking element (16) is shaped and configured to be brought into engagement with a collecting element (28) and a therein placed distal part of the stoma (20).

16 Claims, 8 Drawing Sheets

(56) References Cited

U.S. PATENT DOCUMENTS

| | | | | |
|---|---|---|---|---|
| 2015/0141944 A1* | 5/2015 | Hanuka | ................... | B31B 50/26 |
| | | | | 604/337 |
| 2015/0305916 A1* | 10/2015 | Hanuka | ................. | A61F 5/4405 |
| | | | | 604/333 |
| 2018/0344506 A1* | 12/2018 | Larsen | .................... | A61F 5/448 |

FOREIGN PATENT DOCUMENTS

| | | | | |
|---|---|---|---|---|
| EP | 1795157 A2 * | 6/2007 | ............ | A61F 5/448 |
| EP | 1795157 A2 | 6/2007 | | |
| WO | 90/07311 A1 | 7/1990 | | |
| WO | 02/058603 A1 | 8/2002 | | |
| WO | 2011/031822 A1 | 3/2011 | | |
| WO | WO-2011031822 A1 * | 3/2011 | ............ | A61F 5/448 |
| WO | 2014/181338 A2 | 11/2014 | | |
| WO | 2016/146136 A1 | 9/2016 | | |

* cited by examiner

OSTOMY DEVICE

CROSS-REFERENCE TO RELATED APPLICATIONS

This application claims priority to Danish Application No. PA 2017 00325, filed May 31, 2017 and titled Ostomy Device, the entire contents of which is incorporated herein by reference.

FIELD OF THE INVENTION

The present invention relates to an ostomy device for use in connection with a stoma. More specifically, the invention relates to a device which is suitable for use with a base plate in such a manner, whereby the stoma can be pinched off or blocked for an extended period of time. Subsequently, discharge from the stoma can be collected and emptied without inducing a risk of leakage. Thereby, the risk for skin irritation due to skin contact with faeces or urine is markedly lowered.

BACKGROUND OF THE INVENTION

In connection with certain diseases such as carcinomas of the colon or rectum, the surgical removal of the bowel (colostomy) or small intestine (ileostomy) or parts thereof is often necessary. After surgery, an artificial opening is created on the body allowing faeces or urine, either from the intestine or the urinary tract, to pass through this opening. The discharge from the ileostomy or colostomy is collected in a stoma pouch or bag.

Ostomy can be performed in different ways. The most common ostomies include colostomy, ileostomy and urostomy, respectively. In a colostomy operation, part of the colon is brought to the surface of the abdomen to form the stoma. There are two types of colostomy, namely end colostomy and loop colostomy. End colostomy is typically performed if parts of the colon and rectum have been removed. Loop colostomy is typically performed as a temporary measure in acute situations, and by this operation, part of the colon is lifted above skin level and held in place with a stoma rod. In an ileostomy operation, a part of the small intestine (the ileum) is brought to the surface of the abdomen to form the stoma. An ileostomy is typically created in cases where the end part of the small intestine is diseased and may be performed as either an end ileostomy or a loop ileostomy. End ileostomy is made in cases where part of the colon is removed (or need to rest), and the end of the small intestine is brought to the surface of the abdomen to form the stoma. In a loop ileostomy, a loop of the small intestine is lifted above skin level and held in place with a stoma rod. A loop ileostomy may be temporary and performed to protect a surgical join in the bowel. By urostomy, an isolated part of the intestine is brought onto the surface of the abdomen and the other end is sewn up, and the ureters are detached from the bladder and reattached to the isolated section of the intestine. Because this section of the intestine is too small to function as a reservoir, and there is no muscle or valve to control urination, a urostomy pouch to collect the urine is needed.

It is known in the art to apply base plates (so-called skin plates) in connection with stomas. The base plates are usually fastened or adhered to the skin around the stoma by use of an adhesive. The plates have an orifice/opening (or it may be possible to provide and orifice/opening) through which the stoma can be transferred. Several types of pouches to fit and to be fastened to the base plates are known in the art.

E.g. from EP 1 795 157 A2 an ostomy appliance for fastening to a base plate is known. The ostomy appliance comprises a m attachment ring, the flange of which is permanently attached to the base plate. The ostomy device further comprises means which are suited for detachably attached to the attachment ring, and a cap having a sealing for the stoma, thereby blocking the stoma. In spite of the sealing cap there is still a risk of leakage from the stoma, if not combined with the use of a stoma pouch.

A number of disadvantages are involved with the use of stoma pouches, including the wearer's reduced mobility and possibility of participating in certain activities (e.g. swimming and bathing as well as other activities where clothing closely fitting the body is required). The wearer may understandably prefer the stoma pouch is not visible beneath the clothing.

Therefore, an alternative to the known stoma pouches is desired.

Furthermore, it is desired to provide a ostomy device which eliminates the wearer's need to discharge the stoma pouch for an extended period of time (e.g. for as long as six hours), while at the same time make possible the release of gas from the stoma.

Object of the Invention

It is an object of the present invention to provide an ostomy device that minimises or even eliminates the above disadvantages.

It is also an object of the present invention to provide an ostomy device that enhances the wearer's mobility, and further makes it possible to participate in various activities without revealing the stoma pouch (e.g. swimming and other activities involving closely fitting clothes).

It is further an object of the present invention to provide an ostomy device which enables pinching off or blocking the stoma for an extended period of time (e.g. for as long as six hours), while at the same time enables release of gas from the stoma.

The object of the present invention is achieved by the ostomy device as defined in claim 1. Preferred embodiments are comprised by the dependent claims and further described herein as well as illustrated in the accompanying drawings.

The ostomy device according to the invention is an ostomy device for attachment to (coupling to) a base plate, wherein the ostomy device comprises an attachment ring configured to detachable attachment to the base plate, wherein the ostomy device further comprises elements with means for detachable attachment to the attachment ring, wherein the ostomy device comprises a shield comprising a blocking element, whereby the stoma may be pinched off/blocked, wherein the blocking element is formed and configured to engage with a collecting element and a herein placed distal part of the stoma.

Thereby, the stoma may be pinched off, thus, enabling the wearer's use of the ostomy device for periods of e.g. 2-6 hours without the need for the simultaneous use of a stoma pouch. The blocking element is configured to engage with a collecting element and thereby provide a pressure against the stoma which is thereby pinched off/blocked.

The ostomy device according to the invention may be detachably attached to the base plate through an attachment ring. The ostomy device further comprises elements having means configured for detachable attachment to the attachment ring. These elements may have any suitable shape and geometry.

The shield may have any suitable shape and geometry. However, it may be an advantage that the shield comprises a spherical part (e.g. formed as the surface of a globular structure/dome or an oval structure). The blocking element may suitably have a geometry providing a predefined pressure distribution against the distal part of the stoma, when the blocking element is brought into engagement with a collecting element and the herein placed distal part of the stoma, thereby resulting in the blocking or pinching off of the stoma.

In may be advantageous that the blocking element is displaceably attached to the base plate.

Thereby, the level of blocking or pinching off can be adapted by displacing the blocking element relative to the base plate, since the force and, thus, the pressure by the blocking element acting on the free end of the stoma are defined e.g. by the distance between the blocking element and the base plate. Thus, it is possible to provide a shield having a distance-adjustable blocking element enabling selective adjustment of the blocking of the stoma.

It may be an advantage that the shield is symmetrical, and that the blocking element is centrally placed.

The shield has preferably a convex outer side and a concave part, the latter configured to be placed against the base plate.

It may be an advantage that the ostomy device comprises a closing disc provided with a threaded area, and further that the blocking element is provided with a corresponding threaded area configured to engage with the threaded area of the closing disc. Thereby, the blocking element may be displaced upwards and downwards so as to vary the pressure by the blocking element on the distal end of the stoma in a simple and continuous manner.

It may be an advantage that the closing disc is provided with an internal threaded area extending along an internal cylinder-shaped surface and that the ostomy device comprises a blocking element comprising a cylindrical portion provided with an outer (externally provided) threaded area extending along the outer cylindrical surface of the cylindrical portion.

It may be an advantage that the blocking element is centrally placed on the inner portion of the shield. Thereby, it is possible to provide a shield having a blocking element that can easily be provided with an outer (external) threaded area configured to attachment to a structure (e.g. a closing disc) having a corresponding inner threaded area.

It may be an advantage that the shield covers an area extending along the area of the base plate to which the ostomy device is attached.

Thereby, the shield protects the base plate and ensures that the shield sufficiently covers the area needed.

It may be an advantage that a cavity is present in the central part of the blocking element, wherein the cavity is configured to receive the distal part of a stoma. Thereby, the height of the blocking element (and, thus, the size of the shield may be reduced) may be reduced, since the blocking element may thus receive the part of the stoma to be blocked or pinched off. Thereby, it is possible to place, in the cavity, the stoma as well the free end of the stoma in the collecting element (e.g. a pouch or a condom).

It may be an advantage that the ostomy device comprises a connection member detachably attached to the attachment ring. The application of a detachably mounted/attached connecting element makes it possible to attach and detach the connecting element e.g. when changing collecting elements (e.g. a pouch or a condom). The collecting element may e.g. be attached in a fastening recess provided in the connecting element.

In a preferred embodiment of the invention, the ostomy device comprises a closing disc suited for attachment to the attachment ring or the connecting element. Thereby, it is possible to attach the shield to the closing disc and ensure mechanical attachment to the base plate. It may be preferred that the closing disc is provided with attachment elements for detachable attachment of the shield to the closing disc. It may be an advantage that these attachment elements are configured to enable adjustment of the distance between the closing disc and the base plate.

It may be an advantage that the closing disc comprises a flange having an internal threaded area and comprises an adjacent portion, wherein the flange extends perpendicular to the adjacent portion. Thereby, the stoma can be lead through the opening in the flange, and a flexible collecting element e.g. formed as a pouch (alternatively a condom) may suitably be attached to a ring-shaped attachment recess provided in a connecting element. The collecting element thereby encloses the distal end of the stoma and enables collection of the discharge from the stoma.

It may be an advantage that the shield is provided with one or more grips, e.g. fitting the fingers of the hand. Thereby, the handling of the shield is eased. In a preferred embodiment of the invention, the shield comprises two such finger grips opposed to each other at the periphery of the shield.

It may be an advantage that the lower portion of the closing disc is provided with a number of engagement elements configured to be brought into locking engagement with corresponding openings of an underlying connecting element or an underlying attachment ring. Thereby, it is possible to provide an easy attachment of the closing disc to the underlying connecting element or the underlying attachment ring.

It may be an advantage that the engagement elements are L-shaped. In one embodiment of the invention, the engagement elements are rotatably attached to the closing disc.

In a preferred embodiment of the invention, the L-shaped engagement elements comprise a central portion extending along the longitudinal axis of the closing disc and comprise an engagement structure extending perpendicular to the longitudinal axis of the closing disc.

The closing disc may suitably comprise one, two, three, four, five, six or more engagement elements. In some embodiments of the invention, the engagement elements may be evenly distributed along the lower portion of the adjacent portion of the closing disc. If e.g. three engagement elements are present, the distance between adjacent engagement elements is approximately 120°.

It may be an advantage that the connecting element or the closing disc or both is provided with a number of T-shaped engagement elements configured to be brought in to engagement with corresponding openings of an adjacent attachment ring or an adjacent connecting element. Thereby, it is possible to provide an effective and easy attachment of the closing disc to the attachment ring or the connecting element.

It may be an advantage that the T-shaped engagement elements comprise a central portion extending along the longitudinal axis of the connecting element and comprise two engagement structures extending perpendicular to the longitudinal axis of connecting element. This type of engagement elements makes it possible to rotate the closing disc and, thus, place the closing disc in a number of configurations, whereby the closing disc becomes locked or unlocked relative to the attachment ring or the connecting element.

It may be an advantage that the engagement elements are evenly distributed along the ring-shaped structure of the connecting element.

It may be an advantage that the lower portion of the closing disc is provided with a number of recesses configured to receive protrusions provided on the connecting element.

The number of recesses should preferably at least equal the number of protruding protrusions on the connecting element. The number of recesses may, however, equal the number of protruding protrusions on the connecting elements. Suitably, the number of recesses on the closing disc may be one, two, three, four, five, six or more, depending on the number of protruding protrusions on the connecting element.

The recesses should be provided and distributed such as to angularly correspond to the protruding protrusions on the connecting element, thus, enabling engagement of the protruding protrusions with the recesses.

In one embodiment of the invention, the central portion is rotatably attached to the connecting element, whereby the recesses enable rotation of the engagement elements about the longitudinal axis of the central portion. Thereby, a safe and secure locking is provided by applying simple mechanical means.

It may be an advantage that the attachment ring is provided with openings, each opening being provided with a radial adjacent resilient structure.

The use of a resilient structure for each opening ensures that variations in the different portions are acceptable, while providing easy attachment of the engagement elements to the attachment ring. Furthermore, the resilient structures ensure locking engagement between the openings and the engagement elements.

In one embodiment of the invention, the resilient structure is a wavy/corrugated profile next to the opening and further next to a slit, thus, enabling displacement of the resilient structure, whereby the receipt of a corresponding engagement element of a connecting element is achieved.

In a preferred embodiment, the attachment ring is provided with a centrally placed disc having three openings, each opening provided with a radial adjacent resilient structure.

The openings may advantageously comprise a tangentially extending center structure surrounded by adjacent locking elements configured to provide locking engagement with a connecting element of corresponding engagement elements at the upper portion of the attachment ring.

It may be an advantage that the closing disc comprises an attachment recess configured for receipt and attachment of a collecting element. Thereby, it is possible to attach a collecting element surrounding the distal portion of the stoma, whereby discharge from the stoma may be collected.

It may be an advantage that the attachment recess is annular and has a circular cross-section.

It may be an advantage that the closing disc comprises a peripheral edge extending from the adjacent portion of the closing disc along the longitudinal axis. Thereby, an area is provided enabling the use of an annularly shaped filter.

It may be an advantage that the ostomy device comprises an integrated or built-in filter. Thereby, it is possible to clean/reduce the odour of the gas escaping from the stoma. It may be advantageous to use a carbon filter as this type of filter effectively cleans the gas, thereby markedly reducing the odours from the ostomy device.

It may be an advantage that the connecting element comprises a sealing portion extending along the longitudinal axis of the ostomy device. The sealing portion further ensures retention of discharge gathered by the collecting element attached to the connecting element attached to the attachment recess of the connecting element, which is practical in connection with the removal of the collecting element from the connecting element.

It may be an advantageous to provide one or more engagement profiles for engaging with the shield. The engagement provides may comprise a protruding profile configured to enable rotation of the shield using the engagement profiles.

DESCRIPTION OF THE DRAWINGS

The invention is further explained in relation to the accompanying drawings, where.

DETAILED DESCRIPTION OF THE INVENTION

The accompanying drawings are only intended for illustrating non-limiting embodiments. A number of other embodiments are possible within the scope of the present invention and will readily be recognised by the person skilled in the art. In the following, similar or identical elements of the various embodiments have identical reference numbers.

Figures 1A, 1B:
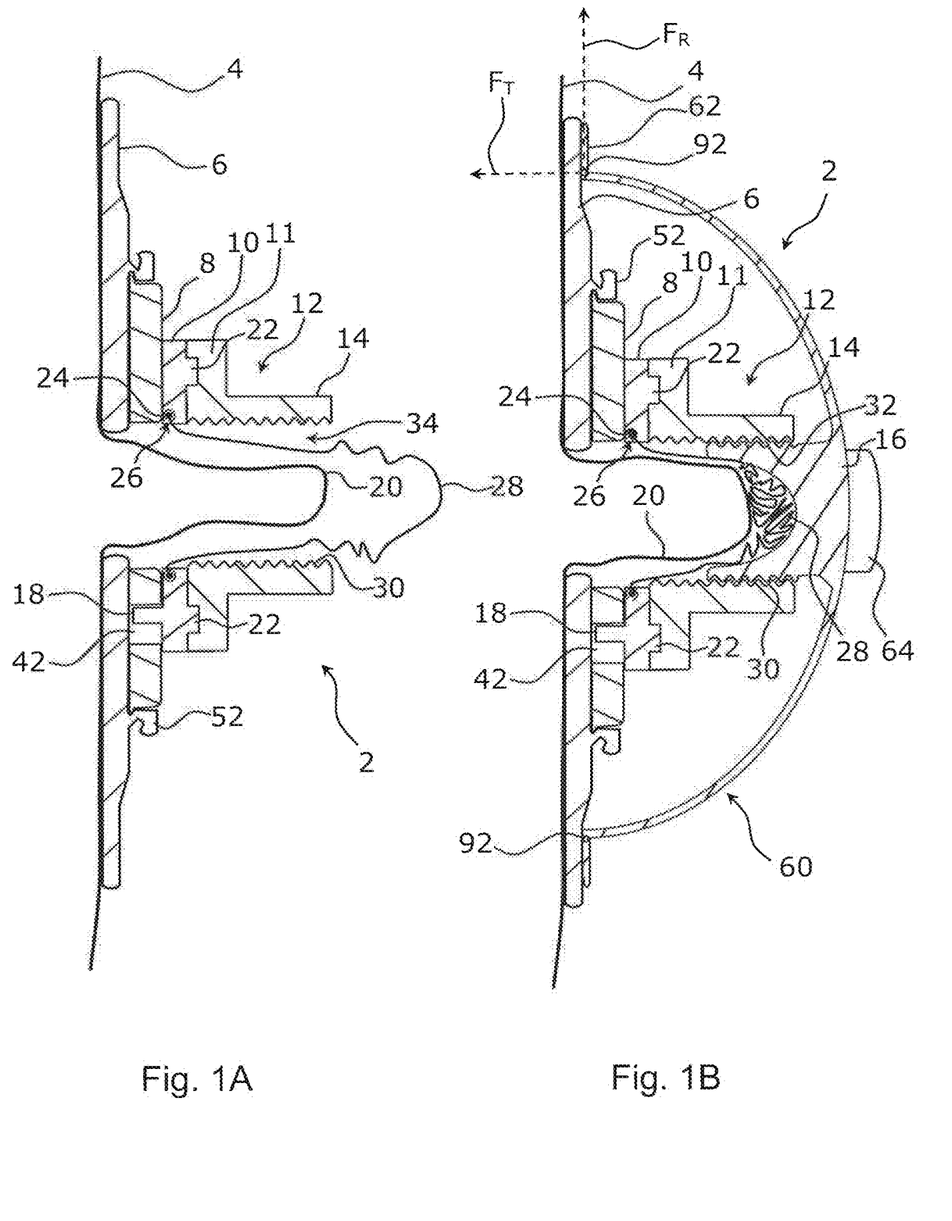
FIG. 1A is a schematically cross-sectional view of a ostomy device according to the invention before the blocking element is attached.
FIG. 1B is a cross-sectional view of the ostomy device shown in FIG. 1A in a configuration, where the blocking element is attached, whereby the stoma is pinched off.

FIG. 1A illustrates a schematically cross-sectional view of an ostomy device 2 according to the invention before the blocking element 16 shown in FIG. 1B is attached. FIG. 1B illustrates a cross-sectional view of the ostomy device 2 shown in FIG. 1A in a configuration, where the blocking element 16 is attached, whereby the stoma 20 is pinched off/blocked to hinder leak of the discharge from the stoma 20.

The ostomy device 2 is attached to a base plate 6, which is fastened to the wearer's skin 4. The ostomy device 2 comprises an attachment ring 8 configured to detachable attachment on the inner portion of a locking flange 52 of the base plate 6, provided in an attachment recess (cf. FIG. 4E). The ostomy device 2 further comprises an annularly-shaped connecting element 10 attached to the attachment ring 8 through the engagement elements 18, said engagement elements 18 configured to be engaged with corresponding openings/apertures 42 of the attachment ring 8 (cf. FIG. 4A and FIG. 4B for further details). The annularly shaped connecting element 10 is provided with protrusions 22 configured to be received by a corresponding aperture (or recess) in the adjacent portion 11 of the closing disc 12 (cf. FIG. 2A and FIG. 2B).

The closing disc 12 comprises a flange 14 having an internal threaded area 30. The flange 13 extends vertically along the adjacent portion 11 of the closing disc 12. The stoma 20 is led through the opening 34 of the ostomy device 2. A flexible collecting element 28 formed as a pouch (alternatively a condom) is attached to an attachment recess 26 provided in the annularly shaped connecting element 10. The collecting element 28 surrounds the distal portion of the stoma 20 and may thus collect the discharge (faeces) excreted from the stoma 20. The ostomy device 2 according to the invention can thereby be applied without a pouch attached to the attachment flange 52. Accordingly, the invention makes it possible to use a "pouch-free ostomy device".

While the stoma 20 shown in FIG. 1A is just surrounded by the surrounding flexible collecting element 28, the stoma 20 is pinched-off as shown in FIG. 1B. In FIG. 1B, a shield 60 is attached to the closing disc 12, the shield 60 comprising a dome-shaped shell (dome) having a centrally placed blocking element 16.

The blocking element 16 pinches against the collecting element 28 and the stoma 20 surrounded by the blocking element 16. Thereby, the stoma 20 is blocked, enabling the wearer of the ostomy device 2 to use the ostomy device 2 for period of e.g. 2-8 hours without a collecting element 28.

Although FIG. 1B seems to show a slit between the back portion of the blocking element 16 and the stoma 20, the back side of the blocking element 16 rests against the collecting element 28 and thereby make a pressure against the stoma 20, which is thus pinched off.

The blocking element 16 comprises an external threaded area 32 fitting the corresponding internal threaded area 30 of the closing disc 12. The blocking element 16 and thus the shield 60 are rotatably attached to the closing disc 12. The blocking element 16 and the shield 60 may by rotation of the shield 60 be moved closer to or further away from the base plate 6. At the topmost part of the shield 60, a protruding profile 64 is provided. This protruding profile 64 functions as a grip which may be used by the wearer of the ostomy device 2 to rotate the shield 60 relative to the base plate 6. Thus, it is possible to vary the distance between the back side of the blocking element 16 and the base plate 6. By rotation of the shield 60, it is thereby possible to vary the force at which the back side of the blocking element 16 acts against the collecting element 28 and the stoma 20, whereby a sufficiently pinching off of the stoma 20 is achieved.

As long as the ostomy device 2 blocks the stoma 20, discharge from the stoma 20 is not excreted. Once the ostomy device 2 is unmounted, the collecting element 28 will fill with discharge from the stoma 20. Subsequently, the collecting element may be unmounted and discarded. An unused collecting element 28 may thereafter be attached, and the ostomy device 2 is ready for further use. The shield 60 comprises et laterally positioned grip 62 for mounting to e.g. a belt (not shown), this being specifically suited for more corpulent wearers. The grips 62 may equally be used for handling of the shield 60. The shield 60 may also be equipped with a sealing element 92 configured to seal the adjacent base plate 6. The sealing element 92 is formed as an O-ring having an annular cross-section. The sealing element 92 may preferably be made from a resilient material, like e.g. a rubber material. The compressive force $F_T$ (tangentially oriented relative to the shield 60), forcing the peripheral portion of the shield 60 against the adjacent base plate 6, compresses the sealing element 92, thereby making the shield 60 as well as the ostomy device waterproof/resistant to water ingress. When the shield 60 is mounted on the stoma 20, the grips 62 of the shield 60 and the thus the sealing element 82 are displaced radially (to the side), whereby a radially oriented force $F_R$ from the shield 60 acts against the sealing element 92 and the grips 62. The shield 60, thus, becomes pre-tightened and thereby able to resist a pressure from water splashing against the shield 60. Accordingly, the shield 60 ensures the underlying or adjacent structures are not brought into contact with the water, whereby the ostomy device 2 is suited for bathing and swimming.

The shield 60 ensures that the wearer of the ostomy device 2 may use the ostomy device 2 in connection with bathing, swimming or other activities, where toileting is not an option.

Figure 2A:
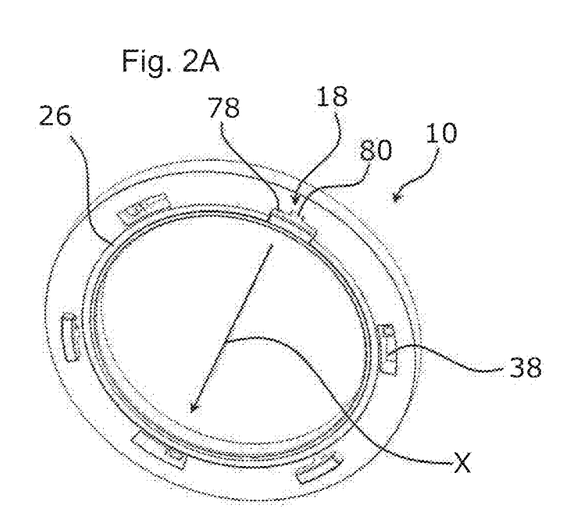
FIG. 2A is a perspective view of a connecting element according to the invention viewed from below.
Figure 2B:
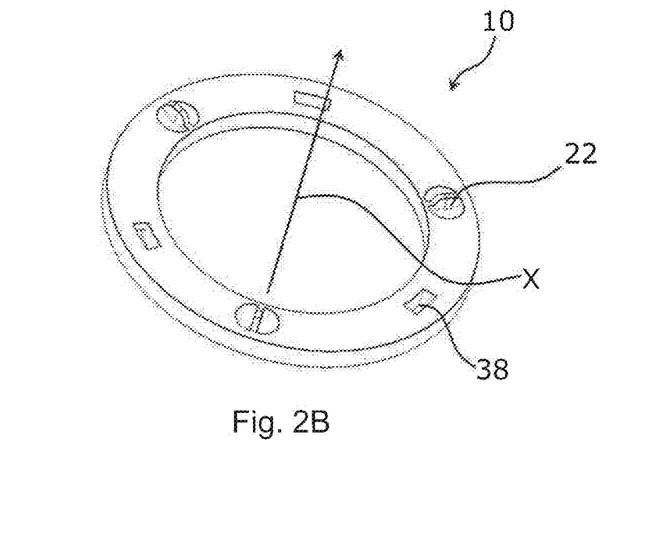
FIG. 2B is a perspective view of the connecting element shown in FIG. 2A viewed from above.

FIG. 2A illustrates, in perspective, a connecting element 10 of the ostomy device 2 viewed from below, whereas FIG. 2B illustrates, in perspective, the connecting element 10 shown in FIG. 2A viewed from above. The connecting element 10 is formed as an annularly shaped structure having a centrally positioned opening. The connecting element 10 is equipped with three openings 38 configured to receive engagement elements 18 (cf. FIG. 2C and FIG. 2D) from an attachment ring 8 positioned below the connecting element 10. The three openings 38 are evenly distributed along the annularly shaped profile of the connecting element 10. Thus, the angle between adjacent openings 38 is approximately 120°. The openings 38 are configured to receive and fixate L-shaped engagement elements 18 of a closing disc 12 positioned above the connecting element 10. The number of openings 38 may be varied. Thus, a connecting element 10 having one, two, three four, five, six or more openings 38 may be provided. The openings 38 may suitably be evenly distributed.

Figures 4A, 4B:
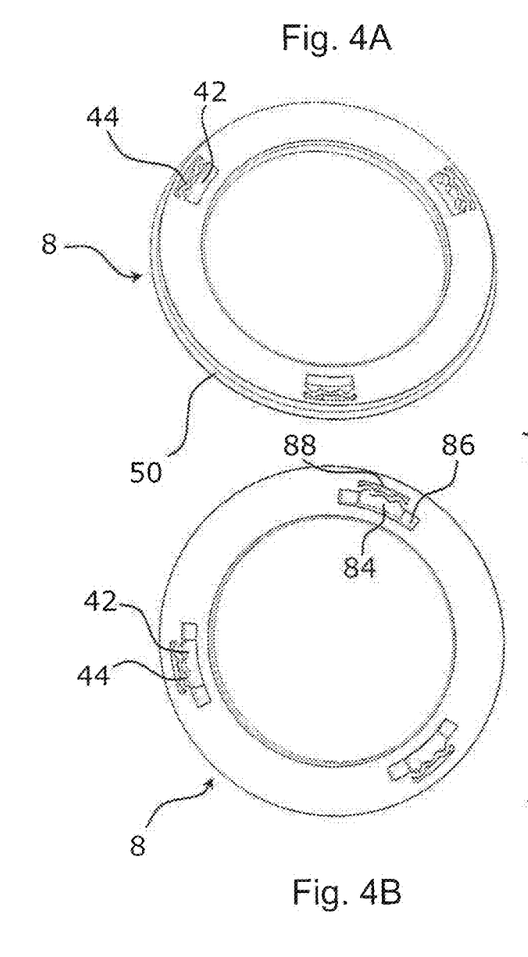
FIG. 4A is a perspective view of an attachment ring according to the invention viewed from above.
FIG. 4B is a perspective view of the attachment ring shown in FIG. 4A viewed from below.

The connecting element 10 further comprises three T-shaped engagement elements 18 configured to be brought into engagement with corresponding openings of an adjacent or underlying attachment ring 8 suited for receiving such engagement elements 18 (cf. FIG. 4A and FIG. 4B). The three engagement elements 18 are evenly distributed along the annularly shaped profile of the connecting element 10. Thus, angle between adjacent connecting elements 10 is approximately 120°. The T-shaped engagement elements 18 comprises a central portion 80 extending along the longitudinal axis X of the connecting elements 10 and two engagement profiles 78 extending perpendicular along the longitudinal axis X of the connecting element 10. It can be seen that the connecting element 10 comprises an annularly shaped attachment profile 26 provided at the under-most side of the connecting element 10. The attachment profile 26 is configured for attachment of a collecting element 28 as shown in FIG. 1A and FIG. 1B. Thus, it is possible to attach the proximal folded end of e.g. a condom to the attachment recess 26 of the connecting element 10.

On the upper side of the connection element 10, upwards protruding protrusions 22 are provided. These protrusions 22 are configured to function as guiding means, when the connecting element 10 is rotated about the longitudinal axis X in connection with the mounting on or demounting from an underlying attachment ring 8. The protrusions 22 may preferably comprise an upright profile extending radially and along the longitudinal axis X. Thereby, it is possible to bring a finger nail into engagement with the profile and thereby provide the required torque in order to mount or demount the connecting element 10 on or from the attachment ring 8. The protrusions 22 may have another shape than the shape shown in FIG. 2B. The number of protrusions 22 may suitably be varied. Thus, it is possible to provide a connecting element having one, two, three, four, five, six or more protrusions 22. The protrusions 22 may suitably be evenly distributed. In one embodiment of the invention, the central portion 80 is rotatably attached to the connecting element 10, whereby the engagement elements 18 may rotated about the longitudinal axis of the central portion 80 using the protrusions 22. Thus, it is possible to provide a very secure locking using very simple mechanical means.

Figure 2C:
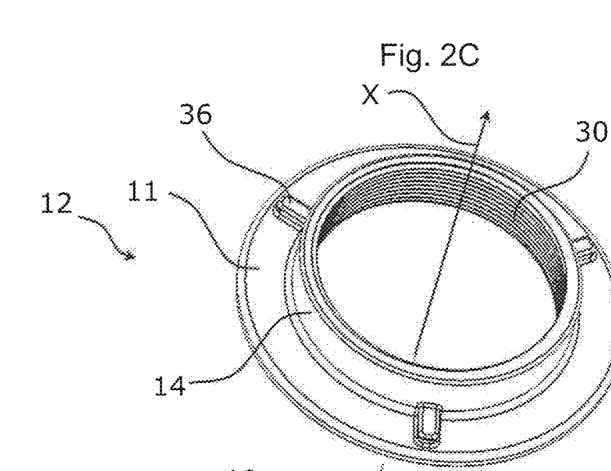
FIG. 2C is a perspective view of a closing disc according to the invention viewed from above.
Figure 2D:
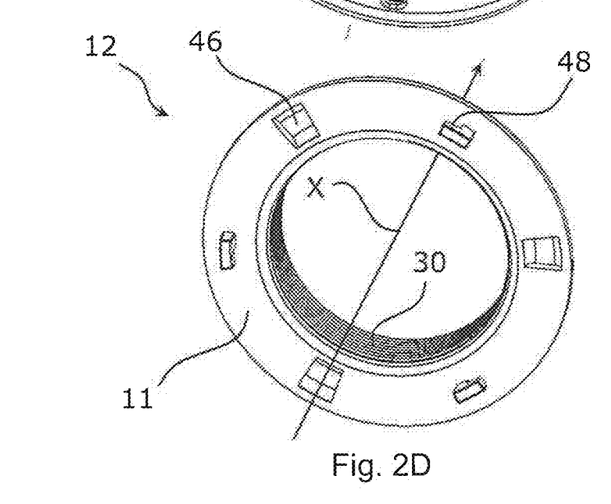
FIG. 2D is a perspective view of the closing disc shown in FIG. 2C viewed from below.

FIG. 2C illustrates, in perspective, a closing disc 12 of the ostomy device 2 according to the invention viewed from above, whereas FIG. 2D illustrates, in perspective, the closing disc 12 shown in FIG. 2C viewed from below. The closing disc 12 comprises a disc-formed adjacent portion 11 configured to be brought into engagement with the underlying or adjacent connecting element 10 corresponding to the connecting element shown in FIG. 2A and FIG. 2B. The closing disc 12 further comprises a protruding flange 14 from the connecting portion 11. The flange 14 is cylindrical and extends along the longitudinal axis X of the closing disc 12. An internal threaded area 30 is provided along the inner side of the flange 14.

On the upper portion of the adjacent portion 11, upwards protruding protrusions 36 is provided, said protrusions 36 being configured to function as a guiding means in connection with mounting or demounting from an underlying connecting element 10. The upwards protruding protrusions 36 comprises an upright profile extending radially and along the longitudinal axis X allowing a finger nail to engage with the profile, thereby providing a sufficiently effective torque to mount or demount the adjacent portion 11 from the underlying connecting element 10.

A slot is provided between the upper part of the adjacent portion 11 and the lower part of the distal portion of the protruding protrusions 36. Thereby, it is possible to place the outer of a finger nail in the slot so as to drag/move the closing disc 12 in the direction of the longitudinal axis. This feature is convenient when removing, demounting or changing the closing disc 12. The number of protruding protrusions 26 may be varied. Thus, it is possible to provide a closing disc 12 having one, two, three, four, five, six or more protruding protrusions 36. It may be an advantage that the protruding protrusions 36 are evenly distributed along the adjacent portion 11 of closing disc 12. In the case of three protruding protrusions 36, the angle between adjacent protrusions 36 is thus approximately 120°.

On the lower portion of the closing disc 12, three L-shaped engagement elements 48 may be provided. The L-shaped engaging elements 48 are configured to be brought into locking engagement with corresponding openings 38 of an underlying connecting element 10 (cf. FIG. 2A and FIG. 2B). The L-shaped engaging elements 48 comprises a central portion 80 extending along the longitudinal axis X of the closing disc 12 and further an engagement profile extending perpendicular to the longitudinal axis of the closing disc 12. More or fewer engagement elements 48 may suitably be provided. Thus, it is possible to provide a closing disc 12 having one, two, three, four, five, six or more engagement elements 48. It may be an advantage that the engaging elements 48 are evenly distributed along the lower portion of the adjacent portion 11 of the closing disc 12. If three engagement elements 48 are present, the angle between adjacent engagement element 48 is thus approximately 120°.

Furthermore, on the lower portion of the closing disc 12, three recesses 46 may be provided. The recesses 46 are configured to receive the protruding protrusions 22 shown on the connecting element 10 and illustrated in FIG. 2B.

The number of recesses 46 should at least equal the number of protruding protrusions 22 of the connecting element 10. The number of recesses 46 may suitably equal the number of protruding protrusions 22 of the connecting element 10. It is possible to provide a closing disc 12 having one, two, three, four, five, six or more recesses 46 depending on the number of protruding protrusions 22 on the connecting element 22. It is, however, a requirement that the recesses 46 are placed/distributed angularly so as to fit the protruding protrusions 22 of the connecting element 10 to enable engagement with the protruding protrusions 22. In FIG. 2D, the recesses 46 are evenly distributed along the lower portion of the adjacent portion 11 of the closing disc 12. Thus, in the case of three protrusions 22, the angle between adjacent recesses 46 is approximately 120°.

Figure 3A:
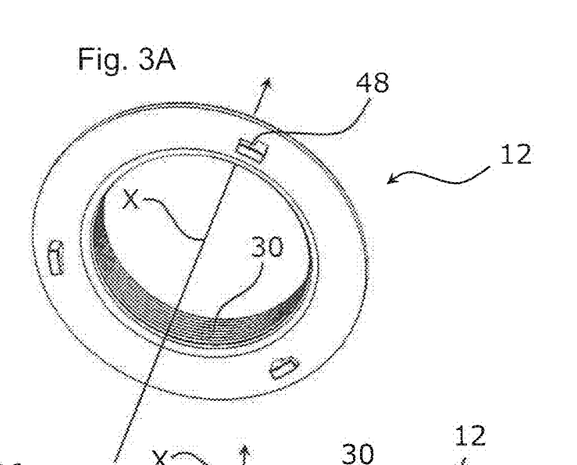
FIG. 3A is a perspective view of a closing disc according to the invention viewed from below.
Figure 3B:
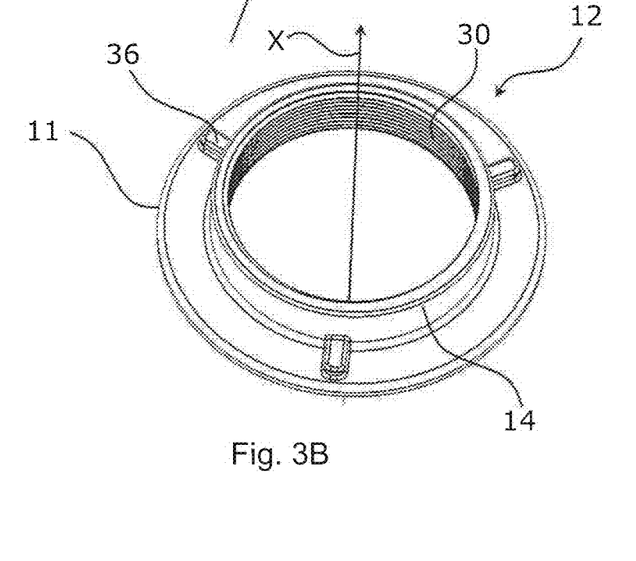
FIG. 3B is a perspective view of the closing disc shown in FIG. 3A viewed from above.

FIG. 3A is a perspective view of a closing disc 12 of an ostomy device 2 according to the invention viewed from below. FIG. 3B is a perspective view from above of the closing disc 12 shown in FIG. 3A. The closing disc 12 is provided with a disc-shaped adjacent portion 11 configured to be brought into engagement with an adjacent, underlying connecting element 10. An underlying connecting element 10 is shown in FIG. 2A and FIG. 2B. The closing disc 12 further comprises a, from the adjacent portion 11, upwards protruding cylindrical flange 14 extending along the longitudinal axis X of the closing disc 12. The inner portion of the flange 14 is provided with an internal threaded area 30. The closing disc 12 essentially corresponds to the closing disc 12 shown in FIG. 2C and FIG. 2D with the exception of the recesses 46 which are shown in FIG. 2D.

Figures 3C, 3D:
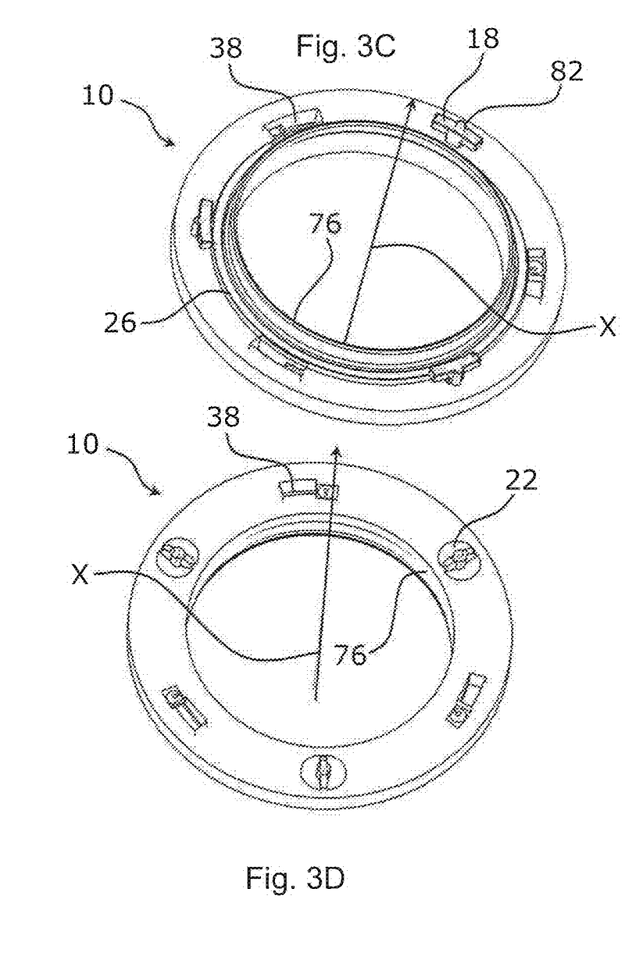
FIG. 3C is a perspective view of a connecting element according to the invention view from below.
FIG. 3D is a perspective view of the connecting element shown in FIG. 3C viewed from above.

FIG. 3C is a perspective view of a connecting element 10 of an ostomy device 2 according to the invention viewed from below, and FIG. 3D is a perspective view of the connecting element 10 shown in FIG. 3C viewed from above. The connecting element 10 corresponds essentially to the connecting element 10 shown in FIG. 2A and FIG. 2B. The connecting element 10 shown in FIG. 3C and FIG. 3C comprises, however, a sealing edge 76 extending along the longitudinal axis X. The sealing edge 76 contributes to retaining discharge collected in the collecting element 28 attached to the attachment recess 26, when removing the collecting element 28 from the connecting element 10.

The one of the three engagement members 18 is provided with a guiding means 82 extending along the longitudinal axis. The guiding means 82 may be suitable for securing a predefined positioning of the connecting element 10 relative to an underlying attachment ring 8 provided with corresponding profile configured to receiving the guiding means 82. The T-shaped engagement members 18 make it possible to provide a double locking system, in which the connecting element 10 may be clicked off engagement with an underlying attachment ring 8 by one simple rotation (one click) and may be brought into locking engagement by an additional rotation (a double-click). The corresponding opening provided in the attachment ring 8 may suitably have a geometry facilitating the click and double-click system.

FIG. 4A is a perspective view of an attachment ring 8 of the ostomy device 2 according to the invention viewed from above, whereas FIG. 4B is a perspective view of the attachment ring 8 shown in FIG. 4A, however, viewed from below.

The attachment ring 8 comprises a centrally located ring-shaped disc provided with three openings 42, each opening 42 provided with a radially adjacent resilient structure 44. The openings 42 comprise a tangentially extending central structure 84 surrounded by corresponding locking elements 86 configured to lockingly engage with the corresponding engagement profiles (cf. 78 in FIG. 2A) of a connecting member 10 on the upper portion of the attachment ring 8. The resilient structure 44 provided for each opening 42 makes it possible to compensate for imperfect fitting of corresponding engagement elements 18 of a connecting member 10 attached to the attachment ring 8. The resilient structure 44 comprises a wavy profile adjacent to the opening 42 and further comprises a slot 88 making displacement of the resilient structure 44 possible, whereby engagement of a corresponding engagement element 48 of a connecting element 10 is possible.

Figures 4C, 4D, 4E, 4F:
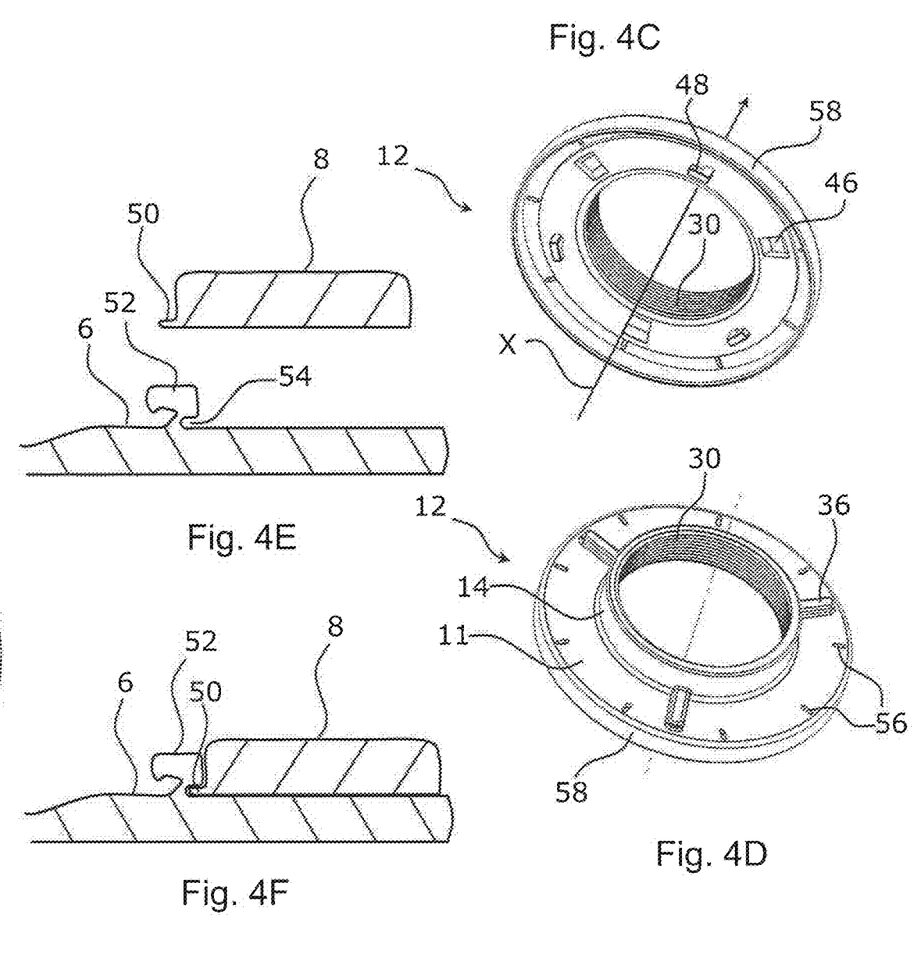
FIG. 4C is a perspective view of a closing disc according to the invention viewed from below.
FIG. 4D is a perspective view of the closing disc shown in FIG. 40 viewed from above.
FIG. 4E is a schematically cross-sectional view of a portion of an attachment ring according to the invention placed on a base plate.
FIG. 4F is a schematically cross-sectional view of the attachment ring shown in FIG. 4E attached to the base plate.

FIG. 4E is a schematic cross-sectional view of a part of an attachment ring 8 of an ostomy device 2 according to the invention placed above a base plate 6, while FIG. 4F is a schematic cross-sectional view of an attachment ring 8 as shown in FIG. 4E attached to the base plate 6. The attachment ring 8 comprises a protruding peripherical located planar ring portion 50 configured to be brought into engagement with a fastening recess/cavity 54 provided on the inner portion of a locking flange 52 of a base plate 6.

FIG. 4C is a perspective view of a closing disc 12 of an ostomy device 2 according to the invention viewed from below, while FIG. 4D is a perspective view of the closing disc 12 shown in FIG. 40, however, viewed from above. The closing disc 12 shown essentially corresponds to the closing disc 12 shown in FIG. 2C and FIG. 2D. The closing disc 12 shown in FIG. 4C and FIG. 4D is, however, provided with cylindrical peripheral edge/enclosing portion 58 extending along the longitudinal axis X as well as a number of ventilation apertures 56 located on the upper part of the adjacent portion 11 of the closing disc 12, thereby differing from the closing disc 12 shown in FIG. 2C and FIG. 2D. The closing disc 12 shown in FIG. 4C and FIG. 4D is configured to receive an annular filter 40, e.g. a carbon filter (cf. FIG. 5A). The carbon filter 40 may suitably be placed peripherally along the inner portion of the peripherical edge 58.

Figure 5A:
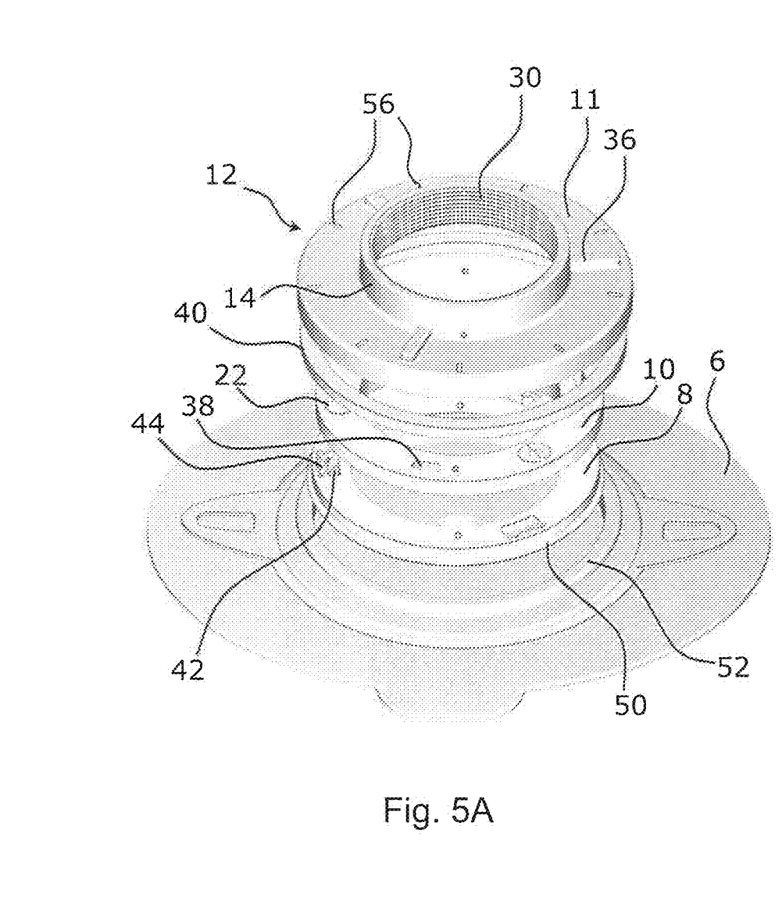
FIG. 5A is a perspective view of an ostomy device according to the invention in a exploded configuration, viewed from above.

FIG. 5A is a perspective view of an ostomy device 2 according to the invention, shown in disassembled configuration and viewed from above. The ostomy device 2 comprises a connecting element 10 configured to be attached to an attachment ring 8 configured to be detachably attached to a fastening recess (cavity) on the inner portion of the locking flange 52 of the base plate 6 (as shown in FIG. 4E). The attachment ring 8 corresponds to the attachment ring 8 shown in FIG. 4A and FIG. 4B and thus comprises openings 42 and adjacent resilient structures 44 provided at a planar upper portion.

Above the attachment ring 8, a planar annularly-shaped connecting element 10 is placed. The connecting element 10 corresponds to the connecting element 10 shown in FIG. 2A and FIG. 2B or FIG. 3C and FIG. 3D. The connecting element 10 comprises openings 38 for receiving the engaging elements (18 see FIG. 5B) of the above placed closing disc 12. The connecting element 10 further comprises upwards protruding protrusions 22.

Above the connecting element 10, an annular carbon filter 40 is provided. The carbon filter 40 is configured to be enclosed by a closing disc 12 placed above the carbon filter 40, A suited closing disc 12 is shown in FIG. 4C and FIG. 4D. The closing disc 12 comprises an adjacent portion 11 having ventilation apertures 56 located along the peripheral portion of the adjacent portion 11. The closing disc 12 further comprises a flange 14 having an internal threaded area 30. The flange 40 is upwards protruding and extend perpendicular to the adjacent portion 11 of the closing disc 12.

Figure 5B:
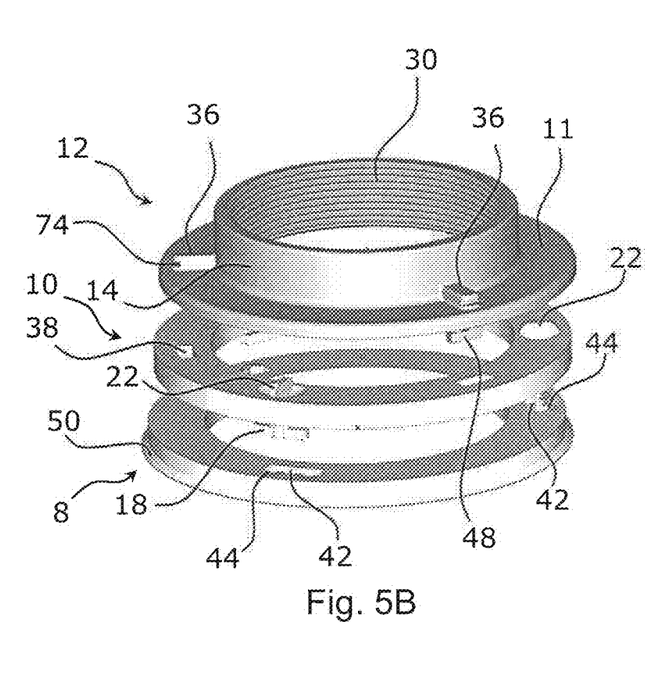
FIG. 5B is a perspective view of portions of an ostomy device according to the invention.

FIG. 5B is a perspective view of parts of the ostomy device 2 according to the invention. The ostomy device 2 comprises an attachment ring 8 corresponding to the attachment ring 8 shown in FIG. 5A.

Above the attachment ring 8, an annularly shaped connecting element 10 is placed. The connecting element 10 comprises a planar upper side provided with openings 38 configured to receive L-shaped engaging elements 48 of a closing disc 12 placed above the planar upper side. The connecting element 10 comprises protruding protrusions 22 suited for acting as guiding means, when rotating the connecting element 10 about its longitudinal axis to mount or demount the connecting element 10 from the underlying attachment ring 8. The connecting element 10 further comprises T-shaped engaging elements 18 configured to be brought into engagement with corresponding openings 42 of the attachment ring 8.

Above the annularly shaped connecting element 10, a closing disc 12 is provided. The closing disc 12 corresponds to the closing disc 12 shown in FIG. 2C and FIG. 2D. The closing disc 12 comprises a disc-shaped adjacent portion 11 configured to engage with the adjacent, underlying connecting element 10. The closing disc 12 is further provided with a, from the adjacent portion 11, upwards protruding cylindric flange 14 extending along the longitudinal axis of the closing disc 12. Along the inner side of the flange 14, an internal threaded area 30 is provided.

On the upper side of the adjacent portion 11, an upwards protruding protrusion 36 is provided. The protrusions 36 are configured to function as guiding means in connection with mounting or demounting from an underlying connecting element 10. The protruding protrusions 36 comprises an upright profile extending radially and along the longitudinal axis, whereby a finger nail may be brought into engagement with the profile in order to provide a sufficiently effective torque for mounting or demounting from an underlying connecting element 10. Between the upper side of the adjacent portion 11 and the underside of the distal portion of the protruding protrusions 36, a slot/notch 74 with a suitable geometry and size is provided. Thereby, it is possible to position the front portion of a finger nail into the slot 74 so as to lead the closing disc 12 along the longitudinal axis, thereby enabling removal, demounting or changing the closing disc 12. The number of protruding protrusions 36 and the number of engaging elements 48 may be varied. Thus, it is possible to provide a closing disc 12 having one, two, three, four five, six or more protruding protrusions 36 and e.g. three engaging elements 48. It may be an advantage that the protrusions 36 as well as the engaging elements 48 are evenly distributed along the adjacent portion 11 of the closing disc 12, whereby the angle between adjacent protrusions 36 and corresponding engaging elements 48 is approximately 120° in the case of three protrusions 36.

Figures 6A, 6B:
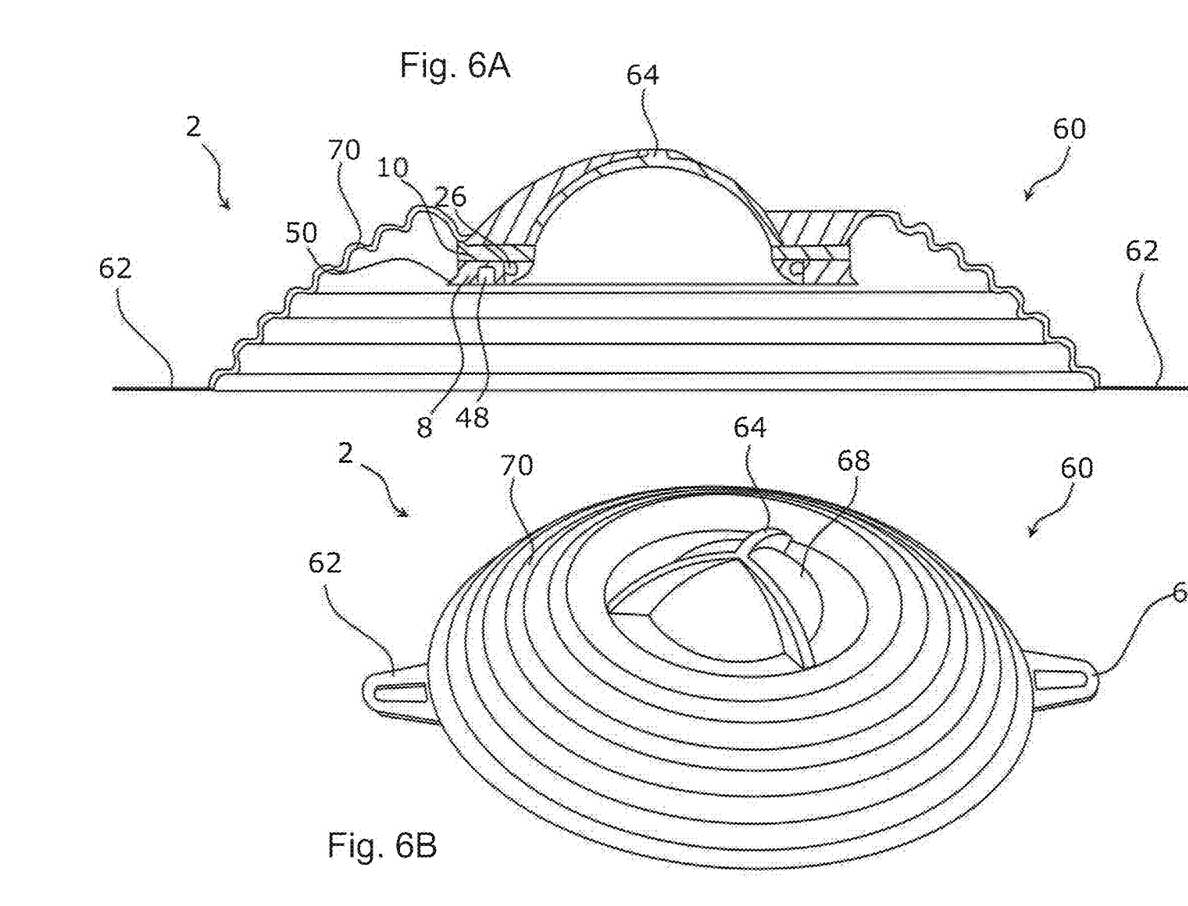
FIG. 6A is a schematically cross-sectional view of an ostomy device according to the invention view from the side.
FIG. 6B is a perspective view of portions of an ostomy device according to the invention.

FIG. 6A is a schematic cross-sectional view of an ostomy device 2 according to the invention, viewed from the side. The ostomy device 2 comprises an attachment ring 8 having a peripherally placed planar ring portion 50 configured to be brought into engagement with a fastening recess 26 provided on the inner portion of a locking flange of the base plate 6. The attachment ring 8 is brought into engagement with an engagement element 38 of the connecting element 10 placed above the attachment ring 8. At the attachment ring 8, an annular attachment recess 26 is provided. The attachment recess 26 is suited and configured for fastening a collecting element corresponding to the collecting element 28 shown in FIG. 1A and FIG. 1B. Thereby, it is possible to fasten the proximal end of e.g. a condom in the fastening recess 26 of the connecting element 10.

The connecting element 10 is fastened or attached to a shield 60, the shield 60 comprising a curvy surface 70 enabling deformation (compression and extension) of the shield 60. On the peripheral portion of the shield 60, two finger grips 62 for attachment to e.g. a belt (not shown) is provided. This may in particular be suited for more corpulent users. The finger grips 62 may further be used for handling the shield 60. On the topmost port of the shield 60, a protruding profile 64 is provided. The profile 64 may be used for rotating the shield 60.

FIG. 6B is a perspective view of parts of the ostomy device 2 corresponding to the ostomy device 2 shown in FIG. 6A. The ostomy device 2 comprises a shield 60 having a curvy surface 70, peripheral finger grips 62 and a centrally placed dome 68 having a protruding profile 64.

Figure 7A:
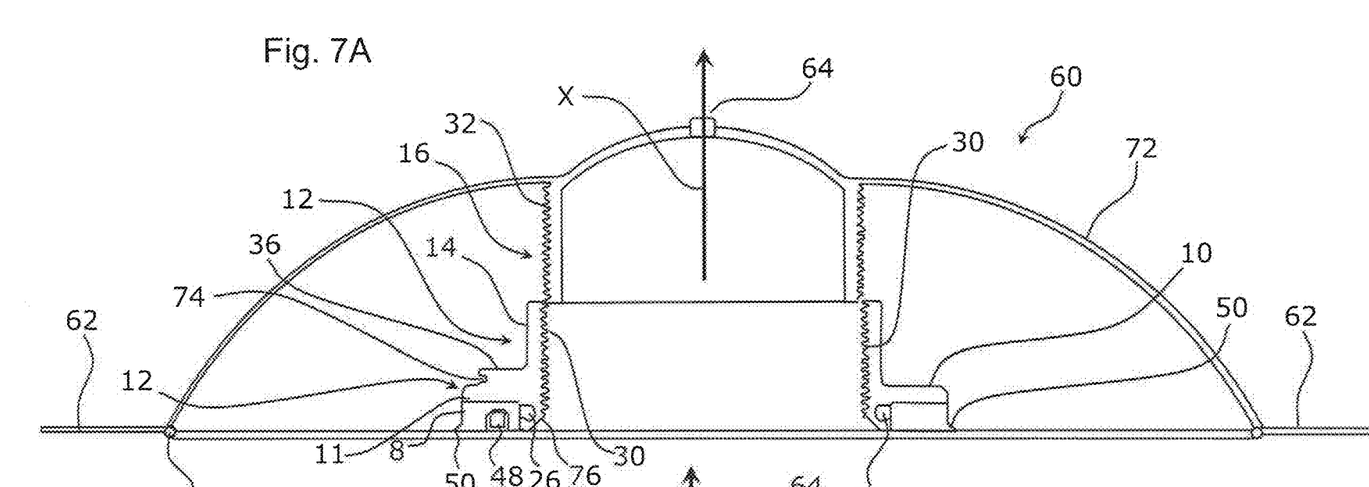
FIG. 7A is a schematically cross-sectional view of an ostomy device according to the invention in a first configuration.
Figure 7B:
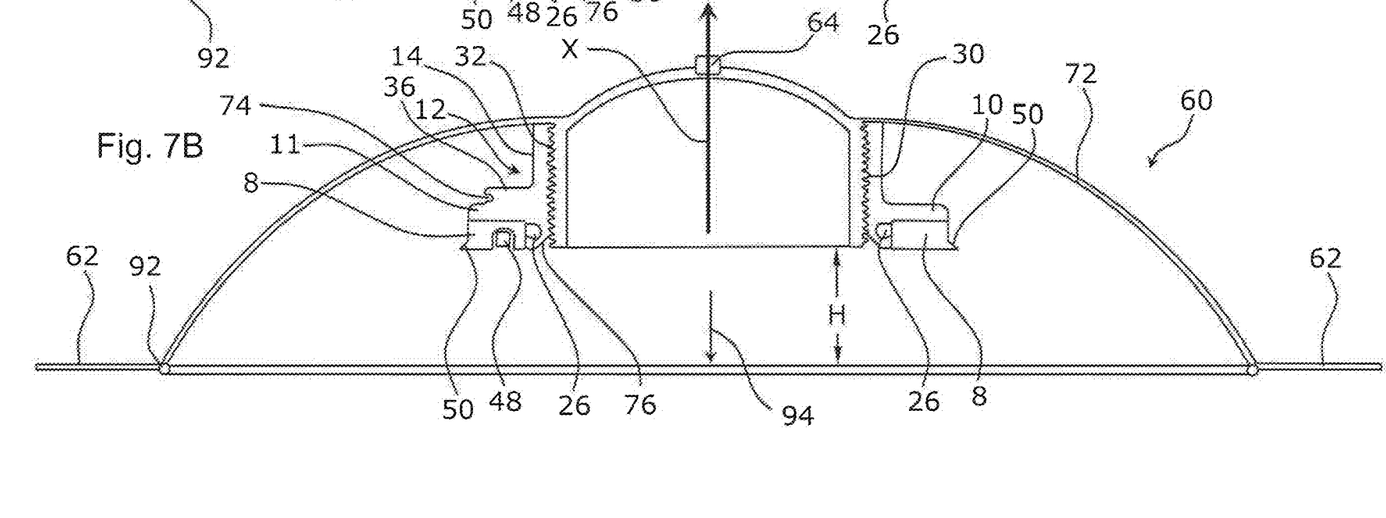
FIG. 7B is a schematically cross-sectional view of the ostomy device shown in FIG. 7A in another configuration.

FIG. 7A is a schematic cross-sectional view of an ostomy device 2 according to the invention, shown in a first configuration, while FIG. 7B is a cross-sectional view of the ostomy device 2 shown in FIG. 7A in another configuration. The ostomy device 2 comprises an attachment ring 8 having a peripheral planar ring portion 50 configured to be brought into engagement with an attachment recess 26 of a locking flange 14 of a base plate 6.

The attachment ring 8 has been brought into engagement with an engagement element 48 of the closing disc 12 placed above the attachment ring 8. The closing disc 12 comprises an annularly shaped attachment recess 26 for fastening/attaching a collecting element 28 as shown in FIG. 1A and FIG. 1B. Thus, it is possible to fasten the proximal folded end of e.g. a condom in the attachment recess 26 of the closing disc 12.

The closing disc 12 is attached or fastened to the attachment ring 8 by means of an engagement element 28, brought into locking engagement with an opening ej vist of the attachment ring 8. The closing disc 12 is provided with a protrusion 36, provided with a notch (slot) 74. A finger nail may be inserted into the notch 74 for moving the closing disc 12 in the longitudinal axis X. The closing disc 12 is provided with an adjacent portion 11 and a cylindrical flange 14, extending perpendicular to the adjacent portion 11 and parallel to the longitudinal axis X. The flange 14 is provided with an internal threaded area 30.

The ostomy device 2 comprises a shield 60 provided with a smooth surface 72, peripheral finger grips 62 and a centrally placed blocking element 16 provided with an outer threaded area 32 configured to be brought into engagement with the inner threaded area 30 of the flange 14. The shield 60 comprises a sealing element 92 shaped as an O-ring (preferably made of a resilient material as e.g. an elastomer such as rubber) and configured to seal against the underlying base plate 6. Once the attachment ring 8 is fastened/attached to the underlying base plate 6 and the blocking element 16 is screwed towards the base plate 6 along the direction 94, the peripheral portion of the shield 60 is forced against the underlying base plate 6 by a compressive force. Thus, the sealing element 92 is compressed, thereby sealing the shield 60 and the ostomy device 2 against water ingress. The displacement of the shield 60 against the stoma 20 results in the radial displacement of the finger grips 62 of the shield 60 and the sealing element 92. Thereby, a radial force from the shield 60 against the sealing element 92 and the finger grips 62 of the shield 60 is provided, whereby the shield 60 is tightened and is able to resist pressure from water acting against the shield 60. The shield 60 further comprises a protruding profile 62 extending from the top of the shield 60, whereby it is possible to rotate the shield 60 relative to the longitudinal axis of the ostomy device 2.

FIG. 7A shows the attachment ring 8 and the thereto attached closing disc 12 in the lowermost position (farthest from the top of the shield 12). FIG. 7B shows the attachment ring 8 and the thereto attached closing disc 12 in the topmost position (closest to the top of the shield 60). In this configuration, the distance H from the underside of the attachment ring 8 and the bottom part of the shield 60 is indicated.

The ostomy device 2 shown in FIG. 7A and FIG. 7B is configured to adjust the placement of the attachment ring 8 and the thereto attached closing disc 12 relative to the top of the shield 60. Thus, it is possible to adjust the placement of the attachment ring 8 and the thereto attached closing disc 12 in order to pinch off the stoma, the distal end of which is enclosed by a collecting element 28 (e.g. a condom) placed in the cavity of the blocking element 16.

Figure 8A:
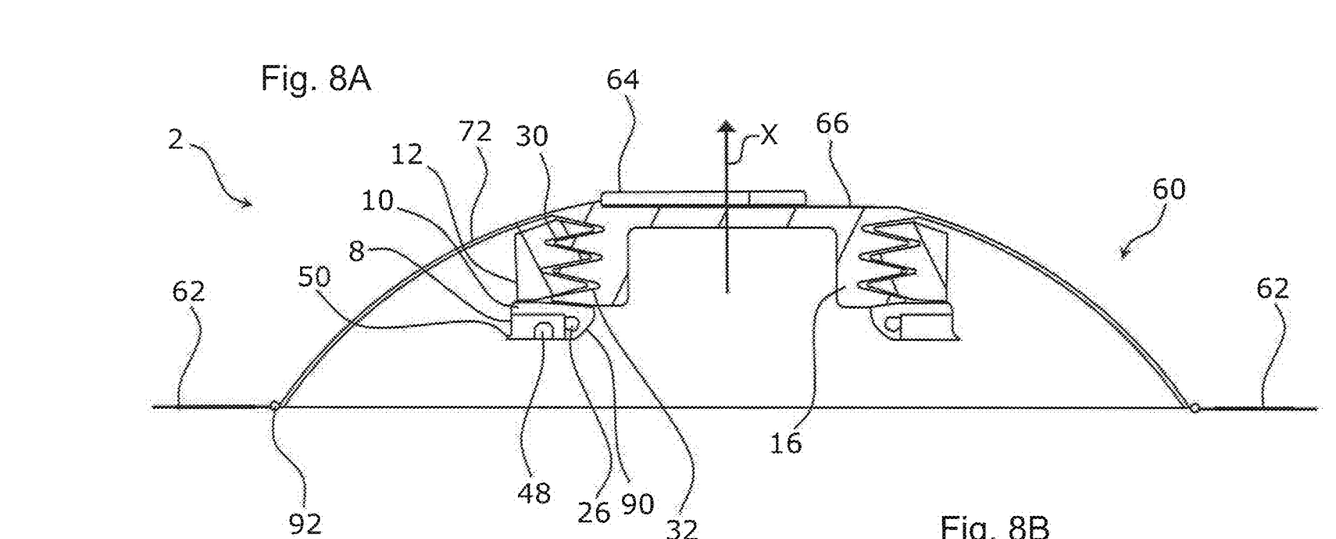
FIG. 8A is a schematically view of an ostomy device according to the invention.

FIG. 8A is a schematic cross-sectional view of an ostomy device 2 according to the invention. The ostomy device 2 comprises a shield 60 having a dome-shaped surface 72 and a finger grip 62 located at the periphery. At the topmost portion of the shield 60, a planar top portion 66 is provided, the planar top portion 66 being provided with a protruding profile 64. Thus, it is possible to rotate the shield 6 about the longitudinal axis X of the ostomy device 2.

The shield 60 comprises a centrally placed blocking element 16 provided with an external threaded area 32 configured to engage with an internal threaded area 30 provided at a closing disc 12 being attached to a connecting element 10 attached to an underlying attachment ring 8. The attachment ring 8 comprises a planar ring portion 50 configured to engage with the inner portion of an attachment recess 26 provided at the locking flange of the base plate 6. The attachment ring 8 is shown to be engage with an engagement element 46 of the connecting element 10 placed above the connecting element 10.

An attachment recess 26 is provided at the connecting element 10 for attachment of a collecting element 28 e.g. as shown in FIG. 1A and FIG. 1B. Using an attachment recess 26 makes it possible to attach, to the attachment recess 26, the proximal folded end of e.g. a condom.

The connecting element 10 is provided with an inner rounded edge 90 for avoiding damage (e.g. by puncturing) to the collecting element 28 when in contact with the connecting element 10.

By rotation of the shield 60 relative to the closing disc 12, the closing disc 12 is displaced along the longitudinal axis X of the ostomy device 2. Thus, it is possible to vary the pressure by which the underside of the blocking element 16 is forced against the free end of the stoma and the pouch or condom enclosing the free end of the stoma. By rotation of the shield 60, it is thus possible to vary the extend of blocking of the stoma. The ostomy device 2 makes it possible to avoid the use of a traditional stoma pouch. Furthermore, the wearer may perform daily and ordinary activities such as swimming and further use closely fitting clothes without the ostomy device 2 being visible.

Figure 8B:
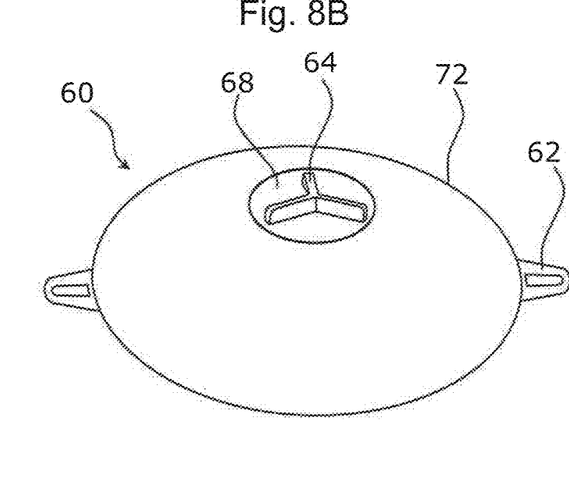
FIG. 8B shows a perspective view of an ostomy device according to the invention.

FIG. 8B is a perspective view of an ostomy device 2 according to the invention. The ostomy device 2 comprises a shield 60 having a dome-shaped surface 72 at the periphery of which two finger grips 62 are provided. At the central portion of the top of the shield 60, a smaller dome 68 is provided, from which a three-parted protruding profile 64 is extending.

| Reference numerials | |
|---|---|
| 2 | Ostomy device |
| 4 | Skin |
| 6 | Base plate |
| 8 | Attachment ring |
| 10 | Connecting element |
| 11 | Adjacent portion |
| 12 | Closing disc |
| 14 | Flange |
| 16 | Blocking element |
| 18 | Engagement element (e.g. L-shaped) |
| 20 | Stoma |
| 22 | Protrusion |
| 24 | Ring porting |
| 26 | Attachment recess |
| 28 | Collecting element |
| 30 | Inner threaded area |
| 32 | External threaded area |
| 34 | Opening |
| 36 | Protrusion |
| 38 | Aperture/opening |
| 40 | Filter |
| 42 | Aperture/opening |
| 44 | Resilient structure |
| 46 | Recess |
| 48 | Engagement element |
| 50 | Planar ring portion |
| H | Hight |
| 52 | Flange |
| 54 | Cavity/recess |
| 56 | Ventilation aperture |
| 58 | Peripheral edge (enclosing portion) |
| 60 | Shield |
| 62 | Finger grip |

| Reference numerials | |
|---|---|
| 64 | Protruding profile |
| 66 | Planar top portion |
| 68 | Dome |
| 70 | Curvy surface |
| 72 | Surface |
| 74 | Notch (slot) |
| 76 | Sealing edge |
| 78 | Engagement profile |
| 80 | Central portion |
| 82 | Guiding means |
| 84 | Central structure |
| 86 | Locking element |
| 88 | Slot |
| 90 | Rounded edge |
| 92 | Sealing element |
| 94 | Direction |
| X | Longitudinal axis |
| $F_T$ | Compressive force |
| $F_R$ | Radially oriented force |

The invention claimed is:

1. An ostomy device for attachment (coupling) to a base plate, wherein the ostomy device comprises an attachment ring configured for detachable attachment to the base plate, wherein the ostomy device further comprises elements having means configured for detachable attachment to the attachment ring, and a shield having a blocking element blocking a stoma, characterised in that the blocking element is shaped and configured to engage with a collecting element and a therein placed distal portion of a stoma, wherein the ostomy device further comprises a closing disc having a threaded area, and in that the blocking element is provided with a corresponding threaded area configured to be brought into engagement with the threaded area of the closing disc, wherein the blocking element is displaceably attached to the base plate, wherein the ostomy device further comprises a sealing element, wherein the ostomy device is arranged and configured to be rotated to be moved closer to the base plate, wherein the base plate, the shield and subsequently the sealing element comes in contact under a compressive force.

2. The ostomy device according to claim 1, characterised in that the closing disc has an internal threaded area along an internal cylinder surface and a cylindrical blocking element having an external threaded area extending along the external cylinder surface.

3. The ostomy device of claim 1 wherein the blocking element is placed centrally on the inner portion of the shield.

4. The ostomy device of claim 1 wherein the shield covers an area extending beyond an area of the base plate to which base plate the ostomy device is attached.

5. The ostomy device of claim 1 wherein the ostomy device comprises a connecting element detachably attached to the attachment ring.

6. The ostomy device of claim 5 wherein the ostomy device comprises a closing disc for attachment to the attachment ring or to the connecting element.

7. The ostomy device according to claim 6, characterised in that the closing disc comprises a flange having an internal threaded area and an adjacent part, where the flange extends perpendicular to the adjacent part.

8. The ostomy device of claim 6, characterised in that a number of engagement elements are provided at the underside of the closing disc, said engagement elements being configured to be in locking engagement with corresponding openings of the underlying connecting element or the underlying attachment ring.

9. The ostomy device of claim 5, characterised in that the connecting element is provided with a number of T-shaped engagement elements configured to be brought into engagement with corresponding openings of the underlying attachment ring.

10. The ostomy device of claim 9 wherein the attachment ring openings are each provided with a radial adjacent resilient structure.

11. The ostomy device of claim 1 wherein the closing disc comprises an attachment recess configured for receiving and attaching a collecting element.

12. The ostomy device of claim 7 wherein the closing disc comprises a peripheral edge extending from the adjacent part of the closing disc along the longitudinal axis of the closing disc.

13. The ostomy device of claim 1 further comprising an integrated filter.

14. The ostomy device of claim 5 wherein the connecting element comprise a sealing edge extending along the longitudinal axis (X) of the ostomy device.

15. The ostomy device of claim 6, characterised in that the connecting element or the closing disc is provided with a number of T-shaped engagement elements configured to be brought into engagement with corresponding openings of the underlying attachment ring or the underlying connecting element.

16. The ostomy device of claim 15 wherein the attachment ring is provided with openings each provided with a radial adjacent resilient structure.

\* \* \* \* \*